United States Patent [19]

Akin et al.

[11] 4,285,976
[45] Aug. 25, 1981

[54] METHOD FOR ACCELERATING AUTOLYSIS OF YEAST

[75] Inventors: Cavit Akin; Rose M. Murphy, both of Naperville, Ill.

[73] Assignee: Standard Oil Company (Indiana), Chicago, Ill.

[21] Appl. No.: 96,789

[22] Filed: Nov. 23, 1979

[51] Int. Cl.³ ............................ A23L 1/28; A23J 1/18; C12C 11/34; C12N 1/06
[52] U.S. Cl. ...................................... 426/60; 426/589; 426/650; 435/256; 435/259; 435/267; 435/272
[58] Field of Search ................... 426/60, 62, 589, 650; 435/256, 259, 267, 272

[56] References Cited

U.S. PATENT DOCUMENTS

| | | | |
|---|---|---|---|
| 1,012,147 | 12/1911 | Nolf | 426/60 X |
| 2,295,036 | 9/1941 | Gorcica et al. | 426/60 X |
| 2,328,025 | 8/1943 | Mead, Jr. et al. | 426/60 X |
| 2,922,748 | 1/1960 | Peppler et al. | 426/60 X |
| 3,961,080 | 6/1976 | Sugimoto et al. | 426/60 |
| 3,975,553 | 8/1976 | Griffon | 426/60 X |
| 4,066,793 | 1/1978 | Eguchi | 426/60 |
| 4,218,481 | 8/1980 | Chao et al. | 426/60 |

FOREIGN PATENT DOCUMENTS 596847 1/1948 United Kingdom .

OTHER PUBLICATIONS

Joslyn et al., Yeast Autolysis, Wellerstein Lab. Communications, vol. 18, No. 62, 1955 (pp. 191–201).
White, J., Yeast Technology, John Wiley & Sons, Inc., N. Y. 1954 (pp. 80–81).

Primary Examiner—David M. Naff
Attorney, Agent, or Firm—Gregory E. Croft; William T. McClain; William H. Magidson

[57] ABSTRACT

Autolysis of yeast slurries is accelerated by the presence of thiamine and/or pyridoxine and by gradually raising the temperature of the yeast slurry to the incubation temperature over a period of time of from about 20 to about 180 minutes.

13 Claims, No Drawings

METHOD FOR ACCELERATING AUTOLYSIS OF YEAST

Yeast autolysis is a well-known process wherein the yeast cell materials are subjected to digestion by their own enzymes. The primary objective is to solubilize the cell materials for subsequent recovery to yield a yeast autolyzate.

The yeast autolyzate is a concentrated form of product which consists of all the autolytically solubilized cellular components (such as amino acids, nucleotides, polypeptides, proteins, glycogen, trehalose, sugars, B-vitamins, and many unidentified flavor compounds) which have been hydrolyzed to smaller molecules by the action of enzymes such as carbohydrases, nucleases, proteases, etc. Its primary use is as a seasoning ingredient for the preparation of sauces, gravies, soups, etc. Because it has a meaty flavor, mainly due to its high glutamic acid content, yeast autolyzate is an inexpensive substitute for meat extracts.

The process of yeast autolysis is a slow reaction. It is induced by heating an aqueous slurry of yeast cells to a temperature where the cells are killed but where the endogenous enzyme activity is still high. Typically temperatures vary between 40°-60° C., with 50°-55° C. being preferred because of the correspondingly higher rate of reaction without damaging the activity of the enzymes. Even at the higher temperature, however, the reaction still requires several days to obtain a suitable degree of digestion, which is usually terminated when approximately 50 percent of the total nitrogen is in the form of alpha-amino nitrogen.

If an autolyzed yeast product is desired, the autolyzed slurry is pasteurized at 80°-90° C. and spray-dried to give the final product. If a yeast autolyzate is the desired product, the autolyzed slurry is cooled and filtered to remove the cell debris and pasteurized. The resulting supernatant is concentrated to yield a paste having a solids content of about 70-80 percent.

To accelerate the autolysis reaction, it is well known to employ one of several plasmolyzing agents. The most popular plasmolyzing agent is table salt. Other plasmolyzing agents such as ethylacetate, amylacetate, chloroform, dextrose, and ethanol.

SUMMARY OF THE INVENTION

It has now been discovered that the autolysis process can be accelerated by the presence of thiamine and/or pyridoxine at concentrations of at least 0.01 weight percent. It has also been discovered that gradually increasing the temperature of the yeast suspension to the incubation temperature over a time span of from about 20 to about 180 minutes also increases the autolysis rate. By utilizing both of these discoveries, autolysis can be accomplished within about 5 hours or less.

EXPERIMENTAL

Because it is most desirable to obtain a rate of autolysis which would be acceptable on a commercial scale, the following examples utilize salt, dextrose, and ethanol in addition to thiamine and pyridoxine in all of the formulations to obtain as fast a rate as possible. Although the presence of such additional plasmolyzing agents is not necessary to observe the increased rate of autolysis due to the presence of the thiamine and/or pyridoxine, such additional plasmolyzing agents are highly preferred for use in conjunction with the thiamine and/or pyridoxine to achieve optimal results.

Although any yeast or other autolyzable organism can be treated in accordance with the process of this invention, compressed baker's yeast (*Saccharomyces cerevisiae*) having a 27-30 percent dry weight was used in all of the examples because of its widespread commercial use.

The following Table I sets forth and summarizes the levels of ingredients and conditions to be used for the autolysis of Baker's Yeast. However, these levels are not intended to limit the scope of the invention. To the extent that the ingredients do not add up to 100%, the remaining balance is water.

TABLE I

|  | Suitable Range | Preferred Range |
|---|---|---|
| Compressed Baker's Yeast | 30-100% | 40-60% |
| Salt | 1-6% | 1.5-4% |
| Dextrose | 0.05-3% | 0.07-0.3% |
| Ethanol | 0.05-4% | 0.07-2.9% |
| Thiamine | 0.01-0.4% | 0.05-0.3% |
| Pyridoxine (optional) | 0.01-0.4% | 0.05-0.2% |
| Holding Temperature | 25-32° C. | 29-31° C. |
| Holding Time | 10-140 min. | 20-40 min. |
| Gradual Temperature Increase Time | 20-180 min. | 30-60 min. |
| Incubation Temperature | 45-58° C. | 50-55° C. |
| Incubation Period | 2-16 hours | 3-5 hours |

EXAMPLE 1

Compressed Baker's Yeast (1.7 Kg.), water (1.7 Kg.), and salt (90 g.) were mixed to form a slurry having a holding temperature below 32° C. The slurry was divided into four equal volumes in one liter beakers. Dextrose (3.75 g.) was added to each beaker and mixed. Ethanol (7.5 ml) was then added to each beaker and mixed. Thiamine was added to three of the four beakers in the amounts of 0.2 g., 0.7 g., and 2.8 g. No thiamine was added to the control. The addition of the thiamine took about 20 minutes. All of the beakers were placed in a water bath and their contents heated to 55° C. within about 40 minutes and maintained at that temperature during the course of the autolysis. At periodic intervals samples were taken from the incubating beakers, centrifuges, and dried to determine the dry weights (solubles). Table II shows the results, which illustrate the increase in solubles formation with increasing levels of thiamine.

TABLE II

| Sample | Thiamine Content (Weight Percent) | Solubles Formed After 75 min. | Solubles Formed After 165 min. |
|---|---|---|---|
| 1 | 0 | 26% | 37% |
| 2 | 0.0355 | 26+% | 38% |
| 3 | 0.0893 | 32% | 41% |
| 4 | 0.357 | 35% | 45% |

EXAMPLE 2

Same as Example 1, except pyridoxine was used in place of thiamine. A similar increase in the rate and amount of soluble matter formation was observed.

EXAMPLE 3

Same as Example 1, except the test suspensions were placed in narrow centrifuge tubes instead of beakers.

The tubes were inserted into a 58° C. water bath and their temperature was raised from the holding temperature to the incubation temperature of 55° C. in less than 5 minutes. A two-hour lag phase occurred and only about 20% solubilization was achieved after 4 hours of incubation. When compared with Example 1, this illustrates the benefits of gradually raising the temperature of the yeast suspension from the holding temperature to the incubation temperature. As previously stated, the time of heating should be from about 20 to about 180 minutes, preferably from about 30 to about 60 minutes.

EXAMPLE 4

On a larger scale, a preferred process scheme would be to dissolve 550 g. of salt in 10 liters of tap water at room temperature (not to exceed 32° C.). Compressed Baker's yeast (10 Kg.) is added to the salt solution while applying mild mixing. The yeast disperses almost immediately to form an easy flowing slurry. The dextrose (100 g.) is then added, which causes carbon dioxide generation almost immediately. Ethanol (200 ml.) and thiamine (20 g.) are then added to the slurry. The mixture is held at room temperature for 30 minutes (the temperature should not exceed 32° C.) and thereafter gradually heated to 50°-55° C. over a period of 40 minutes. The slurry is maintained at this incubation temperature range for about 4 hours. The incubation temperature should not exceed 58° C. at any time to prevent deactivation of the enzymes.

Upon completion of the autolysis, the autolyzed slurry contains essentially two products. One is the insoluble cell residue and the other is the solubilized cell contents. These two products can be physically separated by centrifugation and dried. Individual washing steps can optionally be included for either fraction. The residue can be suspended as a 10% slurry and spray-dried to a powder, whereas the supernatant can by spray-dried directly to yield a yeast autolyzate.

It will be appreciated by those skilled in the art that these examples, shown for purposes of illustration, should not be construed as limiting the scope of this invention, which is defined by the following claims.

We claim:

1. In a process for autolyzing yeasts wherein a yeast slurry is incubated at a temperature of from about 40° to about 60° C. to solubilize the yeast cell materials, the improvement comprising incubating the yeast slurry for from about 2 to about 16 hours in admixture with an additive selected from the group consisting of thiamine, pyridoxine, and a combination of thiamine and pyridoxine at a concentration of at least 0.01 weight percent.

2. The process of claim 1 wherein the concentration of the additive is from about 0.01 to about 0.4 weight percent.

3. The process of claim 1 wherein the autolysis is carried out in the presence of thiamine.

4. The process of claim 3 wherein the concentration of thiamine is from about 0.05 to about 0.3 weight percent.

5. The process of claim 1 wherein the autolysis is carried out in the presence of pyridoxine.

6. The process of claim 5 wherein the concentration of pyridoxine is from about 0.05 to about 0.2 weight percent.

7. The process of claim 1 wherein the yeast slurry is gradually heated to the incubation temperature over the course of from about 20 to about 180 minutes.

8. The process of claim 1 wherein the yeast slurry is gradually heated to the incubation temperature over the course of from about 30 to about 60 minutes.

9. The process of claim 1 wherein the yeast slurry contains at least one plasmolyzing agent in addition to the additive.

10. The process of claim 9 wherein at least one of the plasmolyzing agents is salt.

11. A process for autolyzing an aqueous yeast slurry comprising incubating the slurry at a temperature of from about 50 to about 55° C. for about 2 to about 16 hours in admixture with from about 1 to about 6 weight percent salt, from about 0.05 to about 4 weight percent ethanol, from about 0.05 to about 3 weight percent dextrose, and an additive selected from the group consisting of thiamine, pyridoxine, and a combination of thiamine and pyridoxine at a concentration of at least 0.01 weight percent.

12. The process of claim 11 wherein the slurry is gradually heated to the incubation temperature over a time span of from about 20 to about 180 minutes.

13. The process of claim 12 wherein the yeast is *Saccharomyces cerevisiae*.

* * * * *